United States Patent
Rakocz

(10) Patent No.: US 6,276,934 B1
(45) Date of Patent: Aug. 21, 2001

(54) DENTAL CAMERA

(75) Inventor: Zvi Rakocz, Ramat Hasharon (IL)

(73) Assignee: Miratech Dental Imaging, Ltd., M.P. Hefer (IL)

( * ) Notice: Subject to any disclaimer, the term of this patent is extended or adjusted under 35 U.S.C. 154(b) by 0 days.

(21) Appl. No.: 09/609,423

(22) Filed: Jul. 5, 2000

Related U.S. Application Data

(63) Continuation-in-part of application No. PCT/IL99/00100, filed on Feb. 17, 1999.

(51) Int. Cl.$^7$ ................................ A61C 1/00; A61C 3/00
(52) U.S. Cl. ................................................ 433/29; 433/31
(58) Field of Search .................................... 433/29, 30, 31

(56) References Cited

U.S. PATENT DOCUMENTS

| | | |
|---|---|---|
| 3,884,222 | 5/1975 | Moore . |
| 4,601,284 | 7/1986 | Arakawa et al. . |
| 4,629,425 | 12/1986 | Detsch . |
| 4,727,416 * | 2/1988 | Cooper et al. ..................... 433/29 X |
| 4,915,626 * | 4/1990 | Lemmey ................................ 433/31 |
| 5,139,421 | 8/1992 | Verderber . |
| 5,328,365 * | 7/1994 | Jacoby ................................... 433/29 |
| 5,429,502 | 7/1995 | Cooper et al. . |
| 5,702,249 | 12/1997 | Cooper . |

FOREIGN PATENT DOCUMENTS

| | | |
|---|---|---|
| 30 45 162 | 7/1982 | (DE) . |
| 0 282 832 | 9/1988 | (EP) . |
| WO 96/36294 | 11/1996 | (WO) . |

* cited by examiner

*Primary Examiner*—Nicholas D. Lucchesi
(74) *Attorney, Agent, or Firm*—Weingarten, Schurgin, Gagnebin & Hayes LLP

(57) ABSTRACT

An intraoral viewing device, including a handle and a mirror, fixed to a distal end of the handle, for insertion into the mouth of a patient, such that a first image of the inside of the mouth is viewed by reflection from a surface of the mirror. An image sensor inside the handle receives a second image of the inside of the mouth along a beam axis passing through a plane defined by the surface of the mirror, and generates an electronic image responsive thereto.

40 Claims, 4 Drawing Sheets

DENTAL CAMERA

CROSS-REFERENCE TO RELATED APPLICATIONS

This application is a continuation-in-part of PCT patent application No. PCT/IL99/00100 filed on Feb. 17, 1999, which is incorporated herein by reference.

FIELD OF THE INVENTION

The present invention relates generally to dental equipment, and specifically to intraoral cameras.

BACKGROUND OF THE INVENTION

The dental mirror is a standard part of the dentist's tool kit, providing both direct and indirect views of the patient's mouth during examination and treatment, and aiding in retraction of the muscles of the tongue and inner oral cavity. The dental mirror is an obligatory implement in operative procedures, typically held by the dentist in his or her left hand, while holding another tool in the right.

Recently, intraoral video cameras have been developed, primarily to aid in patient instruction and education. Such cameras enable the dentist to view an enlarged video image of the patient's teeth, as well as to record the image and allow the patient to view the image, if desired. Furthermore, it is possible to save images before and after treatment on a computer, or print them on a video printer. Intraoral cameras known in the art include both stand-alone types and miniature cameras for attachment to a piece of dental equipment, such as a mirror or drill.

U.S. Pat. No. 4,915,626, which is incorporated herein by reference, describes a dental inspection and display device including a fiber optic light guide and micro-camera for attachment to a dental inspection mirror. The device couples to the handle of the mirror and captures the image reflected off of the mirror. The camera and light guide are unwieldy and tend to block the dentist's view.

U.S. Pat. No. 5,429,502, which is incorporated herein by reference, describes an intraoral camera having the general shape of a dental mirror. A camera head located at the distal end of the handle, inside the mouth, captures a direct image of the teeth, instead of the dentist's mirror. The camera head may also be attached to a piece of dental equipment, such as a dental drill, and has facilities for defogging and lighting.

U.S. Pat. No. 4,727,416, which is incorporated herein by reference, also describes a stand-alone electronic video dental camera, shaped similar to a dental mirror, with lighting and defogging facilities. In one embodiment, a mirror is attached to one side of the camera head, inside the mouth. This arrangement is cumbersome, however, and the image captured by the camera will generally not coincide with that seen by the dentist in the mirror.

SUMMARY OF THE INVENTION

It is an object of some aspects of the present invention to provide an improved, integral intraoral camera and dental mirror.

It is a further object of some aspects of the present invention to provide improved apparatus for dental intraoral viewing, which allows substantially similar images to be viewed simultaneously in a dental mirror and on a video monitor.

It is still a further object of some aspects of the present invention to provide intraoral camera apparatus that can be easily sterilized between uses.

In preferred embodiments of the present invention, an intraoral viewing device comprises a dental mirror having a generally central optical aperture and a video camera head, which captures an intraoral image along a beam axis passing through the central optical aperture. Preferably, the beam axis is generally perpendicular to the surface of the mirror, or is slightly angled with respect thereto, so that the image captured by the camera head is substantially overlapping and, most preferably, generally congruent with a direct image seen in the mirror by a dentist using the apparatus.

In some preferred embodiments of the present invention, the video image is captured by an objective lens positioned in an aperture in the mirror. The aperture is preferably in a generally central portion of the mirror, but may alternatively be in another, non-central area or even along a periphery of the mirror. The lens may be positioned in the plane of the mirror, or in front of or behind the plane, depending on optical requirements of the system. Light received through the objective lens is reflected off a turning mirror and conveyed by one or more relay lenses to the camera head, which preferably comprises a CCD detector. Alternatively, a fiber optic image guide may be used to convey the image to the camera head.

Preferably, the camera head is contained in a handle, which is grasped by the dentist, and which is connected to the mirror by a relatively narrow shank, which contains the relay lenses or image guide. The camera head generates video signals, which are transmitted via a cable or wireless link to a video processor and a monitor and/or recording device, as are known in the art.

In some preferred embodiments of the present invention, the handle comprises a light source for intraoral illumination. The light source may be of any suitable type known in the art, such as a miniature tungsten halogen bulb or white light-emitting diode (LED). The light is preferably guided from the light source to the area of the mirror, so as to illuminate the field of view that is seen using the mirror, by a fiber optic light guide in the shank. In a preferred embodiment, the light is conveyed to the area of the mirror by a light guide of the type described in U.S. Pat. No. 5,139,421, which is incorporated herein by reference, wherein the shank connecting the mirror to the handle includes a light guide for conveying the illumination from the light source to the periphery of the mirror.

In a preferred embodiment, the device also includes facilities for lens defogging and cleaning, as are known in the art.

In a further preferred embodiment, the angle of the mirror, and optionally of the objective lens, is adjustable to facilitate a better viewing angle.

The present invention thus provides the dentist with the convenience of handling one instrument, which is in use at all times in operative procedures, rather than juggling between a mirror and a camera. The video image provided by the camera head may be viewed by the dentist during the dental treatment, providing up to 50×magnification relative to the image seen in the mirror. The video image thus aids the dentist in precise, detailed observation, as well as facilitating instruction and education of the patient. At the same time, the dentist may use the device to perform the functions for which conventional dental mirrors are used, including organ retraction in the oral cavity and direct and indirect viewing of the patient's mouth.

There is therefore provided, in accordance with a preferred embodiment of the present invention, an intraoral viewing device, including:

a handle;

a mirror, fixed to a distal end of the handle, for insertion into the mouth of a patient, such that a first image of the inside of the mouth is viewed by reflection from a surface of the mirror; and an image sensor, contained in the handle and optically coupled to receive a second image of the inside of the mouth along a beam axis passing through a plane defined by the surface of the mirror, so as to generate an electronic image responsive to the second image.

In a preferred embodiment, the handle is detachable from the mirror, and the image sensor is withdrawn from the handle for sterilization of the handle. In a further preferred embodiment, the image sensor is rotatable within the handle so as to rotate the electronic image generated thereby.

Preferably, the device includes a shank, intermediate the mirror and the image sensor, wherein the beam axis passes through the shank from the mirror to the image sensor.

Preferably, the device includes relay optics which direct the beam axis through the shank, most preferably including one or more lenses, and/or one or more prisms.

Preferably, the relay optics include a turning optic, which is most preferably positioned behind the plane defined by the surface of the mirror that forms the first image of the inside of the mouth. Most preferably, the turning optic turns the beam axis by an acute angle.

Preferably, the beam axis of the image sensor passes through an aperture in the mirror, most preferably generally at the center of the mirror, that forms the first image of the inside of the mouth. Alternatively, the aperture is adjacent to an edge of the mirror. Preferably, the device includes an objective lens in the aperture for forming the second image on the image sensor.

Preferably, the beam axis along which the second image is received passes through the plane defined by the surface of the mirror in a direction generally perpendicular to the surface of the mirror. Further preferably, the beam axis passes through the plane defined by the surface of the mirror at an acute angle relative to a longitudinal axis of the handle.

Preferably, the first and second images include a common area of the inside of the mouth, and most preferably are generally congruent.

Preferably, the image sensor includes a CCD image sensor.

In a preferred embodiment, the device includes a light source fixed to the handle for illuminating the inside of the mouth.

Preferably, the device is also used for retracting anatomical structures inside the mouth.

In a preferred embodiment, the mirror is disposable.

There is further provided, in accordance with a preferred embodiment of the present invention, an intraoral viewing device, including:

a handle;

a mirror, fixed to a distal end of the handle, for insertion into the mouth of a patient, such that a first image of the inside of the mouth is viewed by reflection from a surface of the mirror; and a camera head, which receives a second image of the inside of the mouth along a beam axis fixed so as to intercept a plane defined by the surface of the mirror at an angle within 30 degrees of a normal to the plane, and generates an electronic image responsive thereto.

Preferably, the beam axis is fixed so as to intercept the plane at an angle within 10 degrees of the normal. Most preferably, the beam axis is fixed so as to intercept the plane substantially normal to the surface.

Preferably, the beam axis intercepting the plane forms an acute angle relative to a longitudinal axis of the handle.

There is further provided, in accordance with a preferred embodiment of the present invention, a method for intraoral imaging, including:

inserting a mirror fixed to the distal end of a handle into the mouth of a patient;

viewing a direct image of the inside of the mouth by reflection from a surface of the mirror; and forming an electronic image of the inside of the mouth by focusing light onto an image sensor contained in the handle, along a beam axis passing through a plane defined by the surface of the mirror.

In a preferred embodiment, the method includes removing the image sensor from the handle during sterilization of the handle. In another preferred embodiment, forming the electronic image comprises rotating the image sensor in the handle so as to rotate the electronic image to a desired orientation.

Preferably, fixing the mirror includes fixing a shank intermediate the mirror and the image sensor, and forming the electronic image includes directing the beam axis through the shank from the mirror to the image sensor.

Preferably, directing the beam axis includes turning the beam axis at an angle relative to a direction along which the beam passes through the plane defined by the surface of the mirror. Further preferably, turning the beam axis includes turning the beam axis at an acute angle relative to the plane defined by the surface of the mirror.

Preferably, forming the electronic image includes focusing the light through an aperture in the mirror.

Preferably, the beam axis passes through the plane defined by the surface of the mirror at an angle within 30 degrees of a normal to the plane. Most preferably, the beam axis passes through the plane in a direction generally perpendicular to the plane.

Preferably, the direct and electronic images include a common area of the inside of the mouth, and most preferably are generally congruent.

Preferably, inserting the mirror into the mouth of a patient includes retracting anatomical structures inside the mouth using the mirror. Preferably the mirror is replaced between uses.

The present invention will be more fully understood from the following detailed description of the preferred embodiments thereof, taken together with the drawings in which:

DETAILED DESCRIPTION OF PREFERRED EMBODIMENTS

Figure 1:
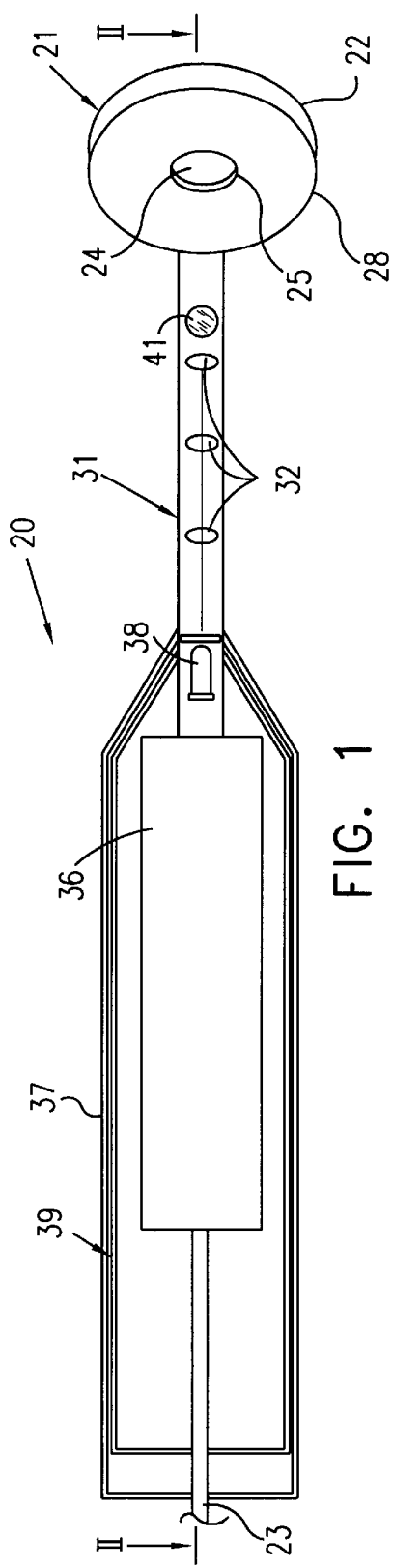
FIG. 1 is a simplified, partly sectional illustration of an intraoral viewing device, in accordance with a preferred embodiment of the present invention.

Reference is now made to FIG. 1, which is a simplified, pictorial illustration of an intraoral viewing device 20, in accordance with a preferred embodiment of the present invention. Device 20 comprises three major sections: a mirror assembly 21, a shank 31, and a handle 37. Handle 37 contains a camera assembly 39, including a video camera head 36, as described below. The three sections are formed together in a shape similar to that of a conventional dental mirror.

Mirror assembly 21 comprises a mirror mount 22, to which a mirror 28, preferably a front-surface mirror, is fixed. An objective lens 24 is fixed in a generally central aperture 25 in mirror 28. Objective lens 24 captures an intraoral image, which is conveyed by a series of relay lenses 32 in shank 31 to camera head 36. Camera head 36 comprises a CCD, preferably a ¼" or ⅓" CCD chip, or other suitable image sensor known in the art. The camera head is preferably coupled via a cable 23 to a video processor and monitor and, optionally, to a video recorder and/or printer, as are known in the art. Preferably, mirror 28 is generally circular, with a diameter of about 22 mm, and lens 24 has a diameter of about 3 mm. Generally speaking, assembly 21 should be about the size of a standard dental mirror, and lens 24 should be large enough to capture sufficient light to enable camera head 36 to form a good quality video image, but not so large as to interfere with direct intraoral viewing by a dentist using mirror 28.

Figure 2A:
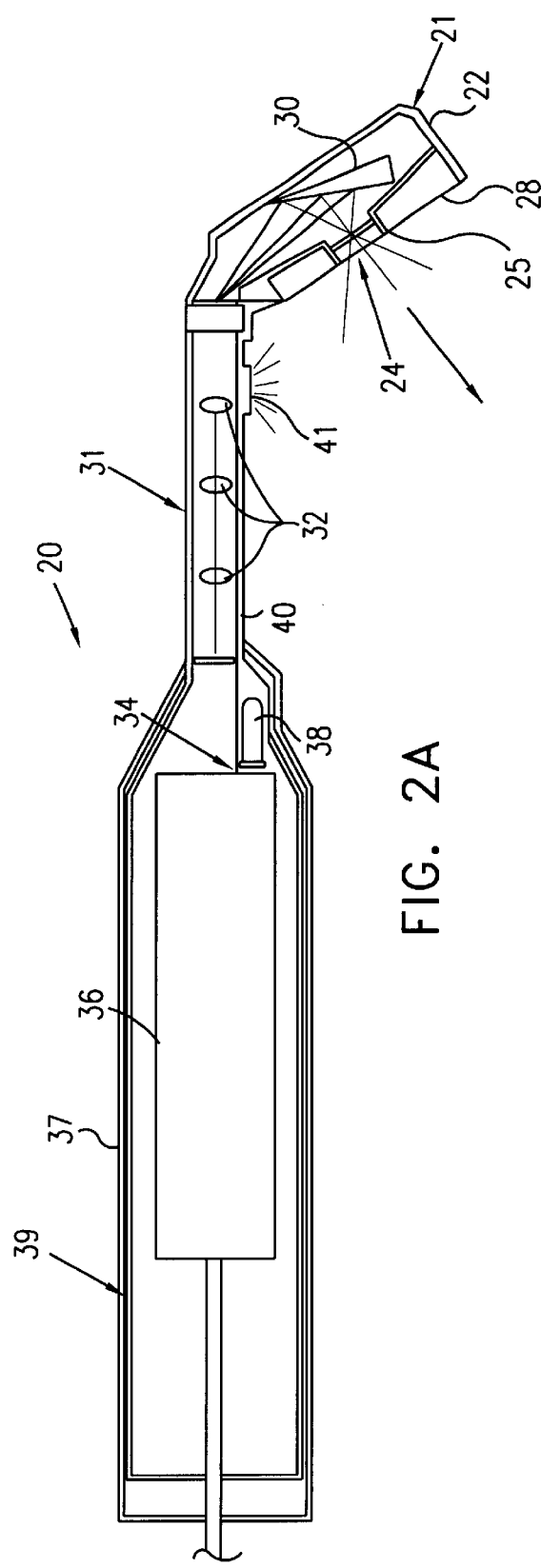
FIG. 2A is a schematic cross-sectional view of the device illustrated in FIG. 1, seen along line II—II.

FIG. 2A is a schematic, sectional view of device 20, seen along line II—II in FIG. 1. As seen in this figure, lens 24 has an optical axis that is generally perpendicular to the reflective surface of mirror 28 and forms an acute angle with shank 31 and handle 37. Light collected by lens 24 is reflected by a turning optic 30, such as a mirror or a prism, in mirror assembly 21 toward relay lenses 32 in shank 31 and from there to camera head 36. Lens 24 thus captures an image that is generally overlapping, and may be substantially congruent, with that seen by the dentist by way of mirror 28, both in terms of viewing angle and, preferably, field of view, unlike combined camera/mirror devices known in the art. Furthermore, because the objective lens and camera head are positioned so as to collect light passing through mirror 28, rather than reflected therefrom, device 20 is less cumbersome than other intraoral camera/mirror devices known in the art, and the camera head does not in any way block the dentist's view of the mouth.

The present invention thus provides the dentist with the convenience of handling one instrument rather than juggling between a mirror and a camera. The video image provided by camera head 36 may be viewed by the dentist during the dental treatment, providing up to 50×magnification relative to the image seen in mirror 28. The video image thus aids the dentist in precise, detailed observation, as well as facilitating instruction and education of the patient. The invention's novel camera functions are provided in addition to the functions of organ retraction in the oral cavity, and direct/indirect view of the patient's mouth, for which conventional dental mirrors are used.

Although lens 24 is shown in the figures as being positioned at the center of mirror 28, it will be appreciated that in alternative embodiments of the present invention, not shown in the figures, the lens may be positioned so that images are conveyed to camera head 36 along a beam axis that is off-center with respect to the mirror, or that passes through the plane of the mirror at or near an edge of the mirror. Furthermore, although the lens as shown in the figures is fixed such that the beam axis is generally perpendicular to the plane of the mirror, those skilled in the art will understand that for optical and/or mechanical convenience, the axis may typically be tilted relative to a normal to the mirror plane by ±10°, or even by as much as ±30°. All such alternative embodiments are considered to be within the scope of the present invention.

Figure 2B:
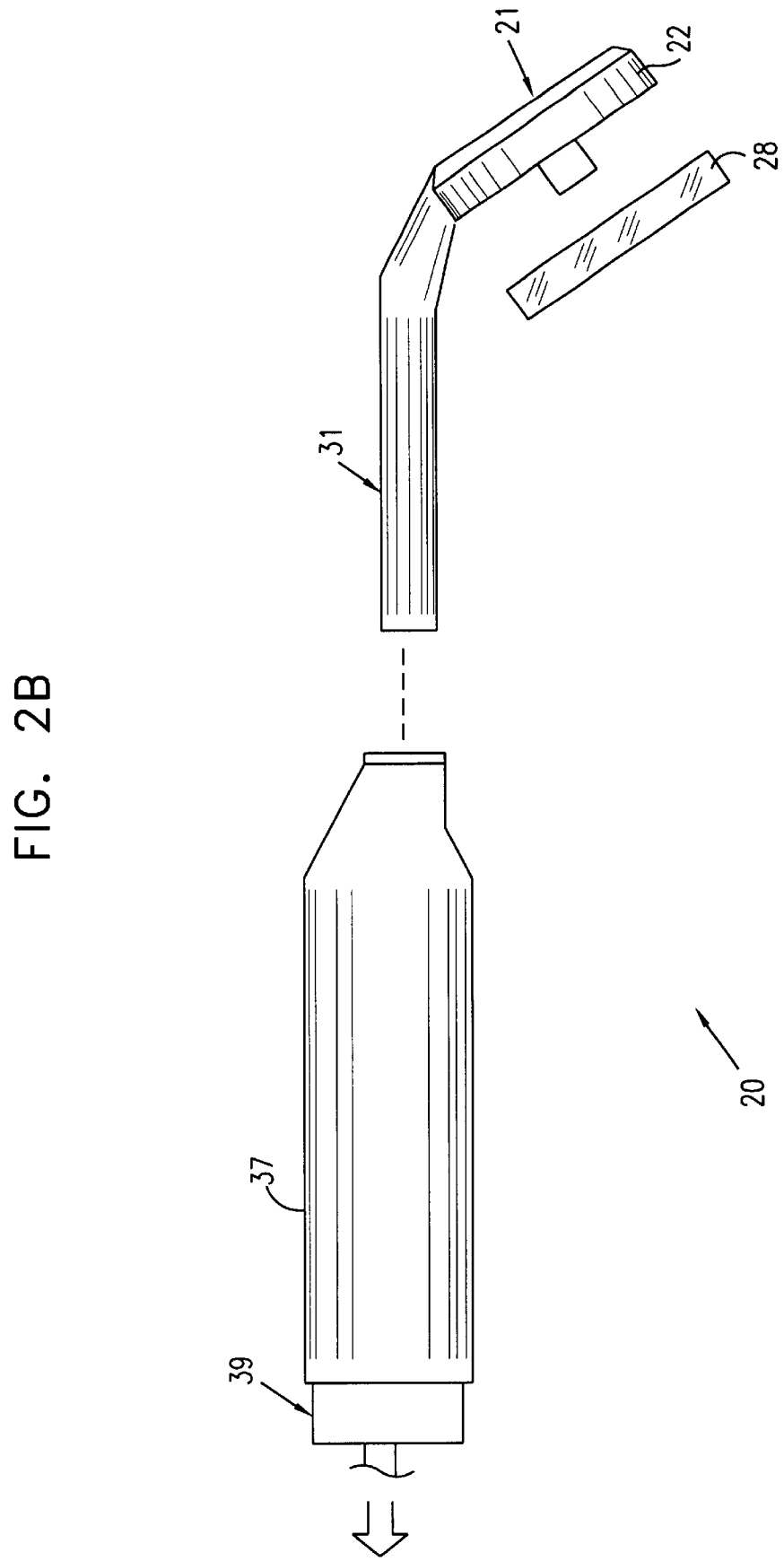
FIG. 2B is a simplified, pictorial illustration showing an exploded view of the device of FIG. 1, in accordance with a preferred embodiment of the present invention.

FIG. 2B is a simplified, pictorial illustration showing an exploded view of device 20, in accordance with a preferred embodiment of the present invention. Mirror assembly 21 and shank 31 are inserted into a patient's mouth during a dental treatment, and consequently must be sterilized or replaced between uses. The outer surface of handle 37 comes into contact with saliva and should generally be sterilized, as well. Therefore, in order to facilitate maintenance and sterilization, device 20 is preferably separable into modules, as shown in FIG. 2B. Mirror 28 is preferably a low-cost, disposable piece made of plastic with a front-surface reflective coating. Mirror mount 22 together with shank 31 may be separated from handle 37 for sterilization, preferably by autoclaving, by either snapping apart or unscrewing. Camera assembly 39 should not generally be subjected to autoclaving, and is therefore removed from handle 37, as shown in FIG. 2B. The handle can then be sterilized, as well. Before reuse, a new mirror 28 is fastened to mount 22, and assembly 21/shank 31 and handle 37 with camera assembly 39 are reassembled, preferably by snapping or screwing together.

Other structures of device 20, not shown in the figures, are also possible. For example, mirror 28 may be an integral part of assembly 21. The entire assembly, together with shank 31, may be autoclavable. Alternatively, the entire assembly may be disposable, as described, for example, in the above-mentioned U.S. Pat. No. 5,139,421.

Figure 3:
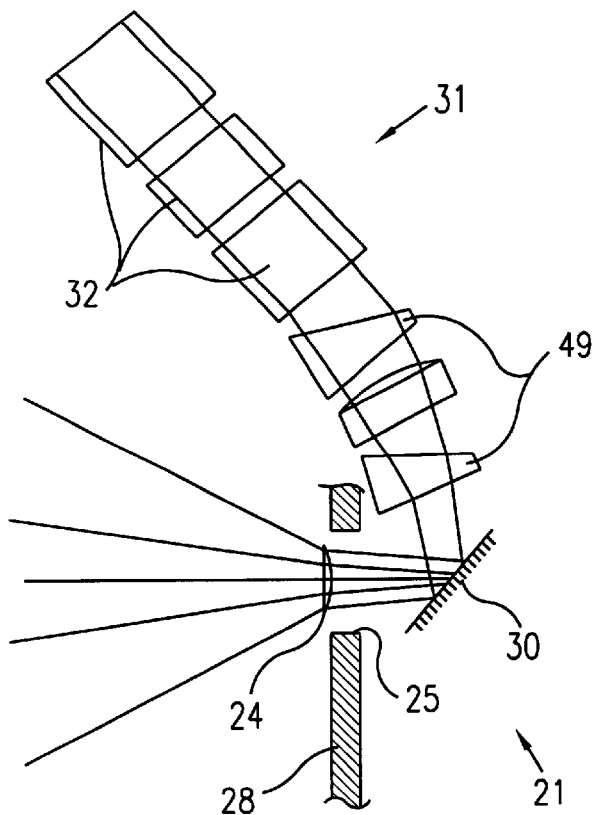
FIG. 3 is a schematic illustration showing details of an optical assembly for use in the device of FIG. 1, in accordance with a preferred embodiment of the present invention.

FIG. 3 is a schematic illustration showing optical details of mirror assembly 21 and shank 31, in accordance with a preferred embodiment of the present invention, corresponding generally to the optical configuration shown in FIG. 2. The optical axis of objective lens 24 is offset and angled relative to the longitudinal axis of shank 31, preferably by about 45°. Optionally, the angle is adjustable for optimal viewing. One or more prisms 49 are interposed in the optical path between reflector 30 and relay lenses 32, in order to bend the optical axis and accommodate the offset of the shank relative to the mirror assembly.

Preferably, relay lenses 32 have a diameter of about 4 mm, and the overall length of shank 31 is about 36 mm. For comfortable viewing inside the mouth, lens 24 preferably has a focal length of about 4.6 mm, and the optical system is optimized for viewing the teeth at a distance of 15 mm from surface 28. However, the optical system of FIG. 3 has sufficient depth of field to allow objects between 5 mm and 150 mm from surface 28 to be viewed without substantial performance deterioration.

In an alternative preferred embodiment, not shown in the figures, some or all of lenses 32 are replaced by a fiber optic image guide, as is known in the art. In this case, prisms 49 are generally not needed. Although FIG. 3 and FIG. 4 (described below) represent preferred embodiments of the optical assembly to be used in device 20, it will be understood that other optical assemblies which perform the same functions of relaying and focusing an image onto camera head 36 are within the spirit of the present invention.

Figure 4:
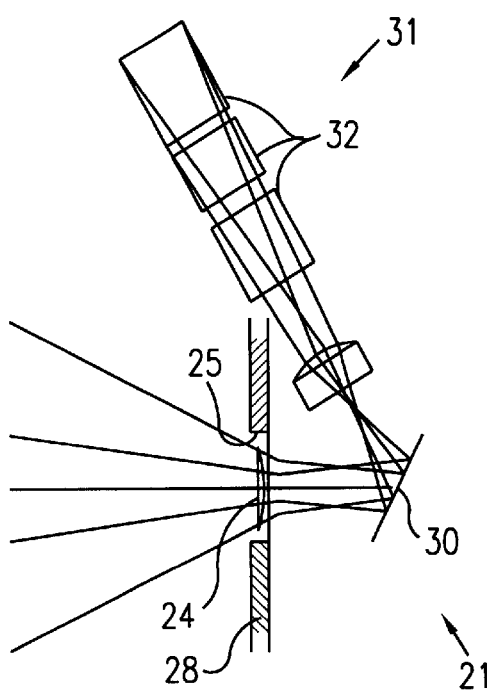
FIG. 4 is a schematic illustration showing details of an optical assembly, in accordance with an alternative preferred embodiment of the present invention.

FIG. 4 is a schematic illustration showing optical details of mirror assembly 21 and shank 31, in accordance with an alternative preferred embodiment of the present invention. In this case, the offset of the shank relative to the mirror assembly is reduced or eliminated, so that prisms 49 are not needed to bend the beam path. In other respects, this embodiment is similar to that shown in FIG. 3.

Returning to FIGS. 1 and 2, it is seen that device 20 preferably comprises a light source 38, for illuminating inside the patient's mouth. Preferably, light source 38 is coupled to a light guide 40, preferably a fiber optic light guide or, alternatively, in the form of a sleeve made of transparent plastic or glass, which conveys and directs the light from source 38 toward the teeth. Light guide 40 ends at a light outlet 41, preferably a prism or lens in shank 31, allowing the guided light to exit and illuminate a section of the patient's mouth in the field of view of mirror 28.

In an alternative preferred embodiment, light guide 40 conveys the light to the periphery of mirror mount 22, in a manner similar to that described in U.S. Pat. No. 5,139,421, which is incorporated herein by reference.

Although not shown in the figures, device 20 may optionally include fixtures for lens defogging or cleaning. In place of or in addition to sleeve 40, shank 31 may include a conduit for conveying a defogging substance, such as either forced air or fluid. The defogging substance flows out of an opening at the distal end of the conduit and defogs or cleans mirror surface 28.

Figure 5:
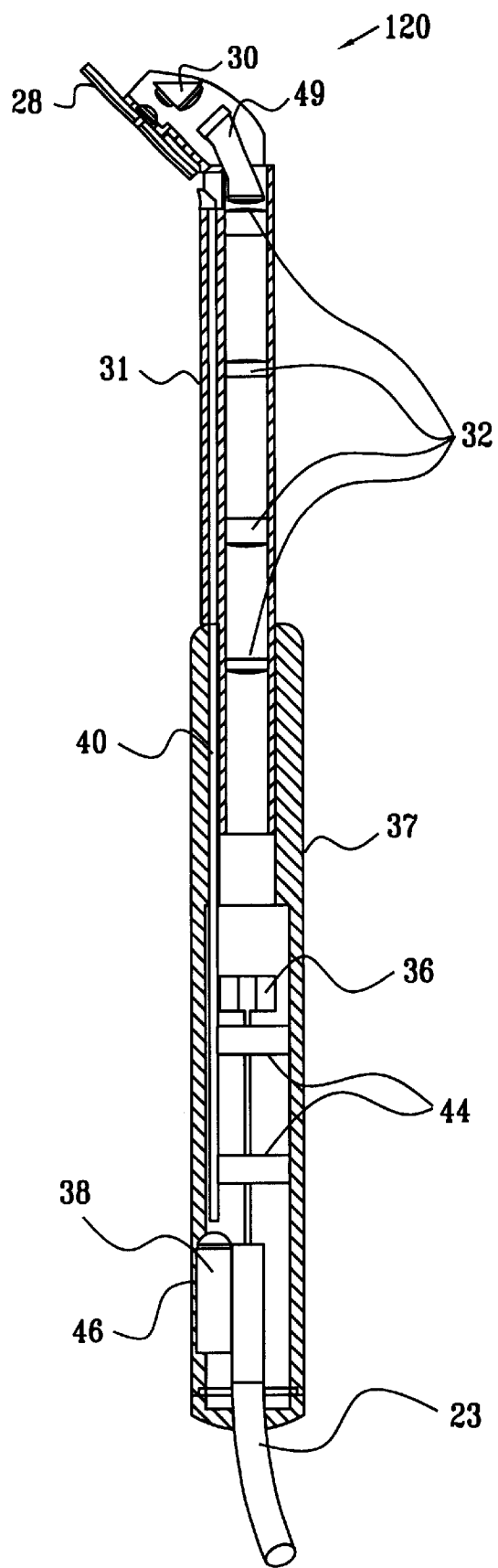
FIG. 5 is a schematic, sectional illustration of an intraoral viewing device, in accordance with another preferred embodiment of the present invention.

FIG. 5 is a schematic, sectional illustration of another intraoral viewing device 120, in accordance with a preferred embodiment of the present invention. Device 120 is functionally similar to device 20, shown in FIG. 1 and described hereinabove. Most of the components of device 120 are marked with the same numbers as are their counterparts in device 20. In addition, however, device 120 includes a motion mechanism 44, which allows camera head 36 to be rotated and moved longitudinally within handle 37. The rotation is important in order to allow the dentist to rotate the image generated by the camera head, so that the image appears right-side-up on a monitor. Longitudinal motion of the camera head allows a certain amount of image zoom and focus control. A radiator 46 is preferably provided adjacent to light source 38 to dissipate excess heat.

It will be appreciated generally that the preferred embodiments described above are cited by way of example, and the full scope of the invention is limited only by the claims.

What is claimed is:

1. An intraoral viewing device, comprising:
    a handle;
    a mirror, fixed to a distal end of the handle, for insertion into the mouth of a patient, such that a first image of the inside of the mouth is viewed by reflection from a surface of the mirror; and
    an image sensor, contained in the handle and optically coupled to receive a second image of the inside of the mouth along a beam axis passing through a plane defined by the surface of the mirror, so as to generate an electronic image responsive to the second image.

2. A device according to claim 1, wherein the image sensor is withdrawn from the handle during sterilization of the handle.

3. A device according to claim 1, wherein the handle is detachable from the mirror.

4. A device according to claim 1, wherein the image sensor is rotatable within the handle so as to rotate the electronic image generated thereby.

5. A device according to claim 1, and comprising a shank, intermediate the mirror and the image sensor, wherein the beam axis passes through the shank from the mirror to the image sensor.

6. A device according to claim 5, and comprising relay optics which direct the beam axis through the shank.

7. A device according to claim 6, wherein the relay optics comprise one or more lenses.

8. A device according to claim 6 wherein the relay optics comprise one or more prisms.

9. A device according to claim 6, wherein the relay optics comprise a turning optic.

10. A device according to claim 9, wherein the turning mirror is positioned behind the plane defined by the surface of the mirror that forms the first image of the inside of the mouth.

11. A device according to claim 9, wherein the turning mirror turns the beam axis by an acute angle.

12. A device according to claim 1, wherein the beam axis of the image sensor passes through an aperture in the mirror that forms the first image of the inside of the mouth.

13. A device according to claim 12, and comprising an objective lens in the aperture for forming the second image on the image sensor.

14. A device according to claim 12, wherein the aperture is generally at the center of the mirror.

15. A device according to claim 12, wherein the aperture is adjacent to an edge of the mirror.

16. A device according to claim 1, wherein the beam axis along which the second image is received passes through the plane defined by the surface of the mirror in a direction generally perpendicular to the surface of the mirror.

17. A device according to claim 1, wherein the beam axis passes through the plane defined by the surface of the mirror at an acute angle relative to a longitudinal axis of the handle.

18. A device according to claim 1, wherein the first and second images include a common area of the inside of the mouth.

19. A device according to claim 18, wherein the first and second images are generally congruent.

20. A device according to claim 1, wherein the image sensor comprises a CCD image sensor.

21. A device according to claim 1, and comprising a light source contained in the handle for illuminating the inside of the mouth.

22. A device according to claim 1, wherein the device is also used for retracting anatomical structures inside the mouth.

23. A device according to claim 1, wherein the mirror is disposable.

24. An intraoral viewing device, comprising:
    a handle;
    a mirror, fixed to a distal end of the handle, for insertion into the mouth of a patient, such that a first image of the inside of the mouth is viewed by reflection from a surface of the mirror; and
    a camera head, contained in the handle, which receives a second image of the inside of the mouth along a beam axis fixed so as to intercept a plane defined by the surface of the mirror at an angle within 30 degrees of a normal to the plane, and generates an electronic image responsive thereto.

A marked-up version of the above amendments showing additions and deletions is attached.

25. A device according to claim 24, wherein the beam axis is fixed so as to intercept the plane at an angle within 10 degrees of the normal.

26. A device according to claim 25, wherein the beam axis is fixed so as to intercept the plane substantially normal to the surface.

27. A device according to claim 24, wherein the beam axis intercepting the plane forms an acute angle relative to a longitudinal axis of the handle.

28. A method for intraoral imaging, comprising:

inserting a mirror fixed to the distal end of a handle into the mouth of a patient;

viewing a direct image of the inside of the mouth by reflection from a surface of the mirror; and forming an electronic image of the inside of the mouth by focusing light onto an image sensor contained in the handle, along a beam axis passing through a plane defined by the surface of the mirror.

29. A method according to claim 28, and comprising removing the image sensor from the handle during sterilization of the handle.

30. A method according to claim 28, wherein forming the electronic image comprises rotating the image sensor in the handle so as to rotate the electronic image to a desired orientation.

31. A method according to claim 28, wherein fixing the mirror comprises fixing a shank intermediate the mirror and the image sensor, and wherein forming the electronic image comprises directing the beam axis through the shank from the mirror to the image sensor.

32. A method according to claim 31, wherein directing the beam axis comprises turning the beam axis at an angle relative to a direction along which the beam passes through the plane defined by the surface of the mirror.

33. A method according to claim 32, wherein turning the beam axis comprises turning the beam axis at an acute angle relative to the plane defined by the surface of the mirror.

34. A method according to claim 28, wherein forming the electronic image comprises focusing the light through an aperture in the mirror.

35. A method according to claim 28, wherein the beam axis passes through the plane defined by the surface of the mirror at an angle within 30 degrees of a normal to the plane.

36. A method according to claim 28, wherein the beam axis passes through the plane in a direction generally perpendicular to the plane.

37. A method according to claim 28, wherein the direct and electronic images include a common area of the inside of the mouth.

38. A method according to claim 37, wherein the direct and electronic images are generally congruent.

39. A method according to claim 28, wherein inserting the mirror into the mouth of a patient comprises retracting anatomical structures inside the mouth using the mirror.

40. A method according to claim 28, wherein inserting the mirror into the patient's mouth comprises replacing the mirror between uses.

* * * * *

UNITED STATES PATENT AND TRADEMARK OFFICE
CERTIFICATE OF CORRECTION

PATENT NO.    : 6,276,934 B1
DATED         : August 21, 2001
INVENTOR(S)   : Zvi Rakocz It is certified that error appears in the above-identified patent and that said Letters Patent is hereby corrected as shown below:

<u>Title page,</u>
After Item [22], insert the following:

-- [30] Foreign Application Priority Data:    February 19, 1998    (IL)    123369 --

<u>Column 8,</u>
Lines 57-58, please delete "A marked-up version of the above amendments showing additions and deletions is attached."

Signed and Sealed this

Seventeenth Day of September, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.     : 6,276,934 B1
DATED          : August 21, 2001
INVENTOR(S)    : Zvi Rakocz It is certified that error appears in the above-identified patent and that said Letters Patent is hereby corrected as shown below:

<u>Title page,</u>
After Item [22], insert the following:

-- [30] Foreign Application Priority Data:   February 19, 1998   (IL)   123369 --

<u>Column 8,</u>
Lines 57-58, please delete "A marked-up version of the above amendments showing additions and deletions is attached."

Signed and Sealed this

Fifteenth Day of October, 2002

*Attest:*

*Attesting Officer*

JAMES E. ROGAN
*Director of the United States Patent and Trademark Office*